United States Patent [19]

Ehrenfreund

[11] Patent Number: 5,210,100

[45] Date of Patent: May 11, 1993

[54] PHENYLBENZOYLUREAS

[75] Inventor: Josef Ehrenfreund, Allschwil, Switzerland

[73] Assignee: Ciba-Geigy Corporation, Ardsley, N.Y.

[21] Appl. No.: 427,940

[22] Filed: Oct. 25, 1989

Related U.S. Application Data

[63] Continuation of Ser. No. 302,052, Jan. 25, 1989, abandoned, which is a continuation of Ser. No. 767,985, Aug. 21, 1985, abandoned.

[30] Foreign Application Priority Data

Aug. 31, 1984 [CH] Switzerland ............................ 4179/84

[51] Int. Cl.$^5$ .................... A01N 47/28; C07C 275/30
[52] U.S. Cl. ........................................ 514/594; 564/44
[58] Field of Search ................... 564/44, 23; 514/594, 514/584

[56] References Cited

U.S. PATENT DOCUMENTS 3,748,356  7/1973  Wellinga et al. ...................... 564/44

FOREIGN PATENT DOCUMENTS 23884    2/1981  European Pat. Off. .............. 564/44
107214   5/1984  European Pat. Off. .
2726684  1/1979  Fed. Rep. of Germany .
3217619 11/1983  Fed. Rep. of Germany ........ 564/44
2106499  4/1983  United Kingdom .................. 564/44
2106501  4/1983  United Kingdom .................. 564/44

Primary Examiner—Carolyn Elmore
Assistant Examiner—Shailendra Kumar
Attorney, Agent, or Firm—Kevin T. Mansfield; Edward Mc. Roberts

[57] ABSTRACT

The invention relates to novel N-[3-halo-4-(hexafluoropropoxy)-5-trifluoromethyl]phenyl-N'-benzoylureas of the formula

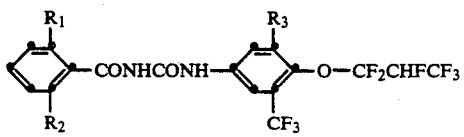

wherein $R_1$ is hydrogen or halogen and $R_2$ and $R_3$ are halogen, to a process and intermediate for the preparation of these compounds, and to compositions containing them for use in pest control, in particular for controlling insects and representatives of the order Acarina that attack plants and animals. The novel compounds exhibit in particular larvicidal activity.

4 Claims, No Drawings

PHENYLBENZOYLUREAS

This application is a continuation of application Ser. No. 302,052, filed Jan. 25, 1989, abandoned, which is a continuation of application Ser. No. 767,985, filed Aug. 21, 1985, abandoned.

The present invention relates to novel N-[3-halo-4-(hexafluoropropoxy)-5-trifluoromethyl]phenyl-N'-benzoylureas, to the preparation thereof and to the use thereof in pest control.

The compounds of this invention have the formula I

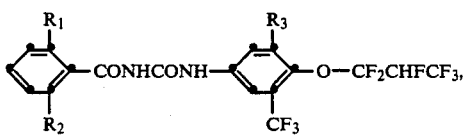

wherein $R_1$ is hydrogen or halogen and $R_2$ and $R_3$ are halogen.

Within the scope of this invention, halogen will be understood as meaning fluorine, chlorine and bromine, in particular fluorine and chlorine for $R_1$ and $R_2$ and chlorine and bromine for $R_3$.

On account of their activity as pesticides, preferred compounds of formula I are those wherein $R_1$ is hydrogen, fluorine or chlorine, and $R_2$ is fluorine or chlorine, and $R_3$ is chlorine.

To be singled out for special mention are also those compounds of formula I, wherein $R_1$ is hydrogen, fluorine or chlorine, $R_2$ is fluorine or chlorine, and $R_3$ is bromine.

The compounds of formula I can be prepared by methods which are known per se (q.v. for example German Offenlegungsschrift specifications 2 123 236 and 2 601 780 and European patent application 13 414).

Thus, for example, a compound of formula I may be obtained by reacting
a) a compound of formula II

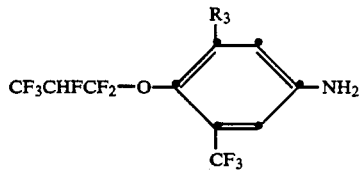

with a compound of formula III

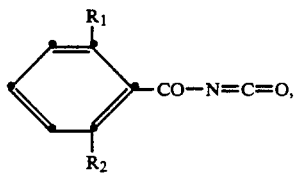

b) a compound of formula IV

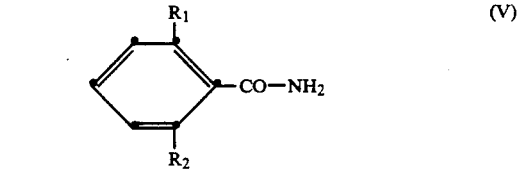

with a compound of formula V

or c) a compound of formula II with a compound of formula VI in which formulae II, III, IV, V and VI above $R_1$, $R_2$ and $R_3$ are as defined for formula I and R is a lower or average $C_1$-$C_8$-alkyl radical which may be substituted by halogen, preferably chlorine.

The above processes a) to c) can preferably be carried out under normal pressure and in the presence of an organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, especially benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process a) is normally carried out in the temperature range from $-10°$ to $100°$ C., preferably from $15°$ to $25°$ C., if desired in the presence of an organic base, e.g. triethylamine. Process b) is carried out in the temperature range from $0°$ to $150°$ C., preferably at the boiling point of the solvent employed and, if desired, in the presence of an organic base such as pyridine, and/or with the addition of an alkali metal or alkaline earth metal, preferably sodium. For the reaction of the urethane of formula VI according to process c), a temperature range from about $60°$ to the boiling point of the reaction mixture is preferred, and the solvent employed is preferably an aromatic hydrocarbon such as toluene, xylene, chlorobenzene and the like.

The starting materials of formulae II, III, IV, V and VI are known or, if novel, can be prepared by methods analogous to known ones. The substituted anilines of formula II are novel compounds which likewise constitute an object of the invention and can be prepared according to methods known in the literature e.g. by hydrogenating 2-halo-6-trifluoromethyl-4-nitrophenol (q.v. J. Org. Chem. 27 (1962), 4660), in the presence of acetic anhydride, and etherifying the resultant 2-halo-6-trifluoromethyl-4-acetaminophenol with hexafluoropropylene in analogy to the method described in Am. Soc. 73 (1951), 5831. The N-acetyl group is subsequently split off in conventional manner to give the aniline of formula II.

It has been found that the compounds of this invention have excellent properties as pesticides while being well tolerated by plants and having low toxicity to warm-blooded animals. They are particularly suitable for controlling insects and representatives of the order Acarina that attack plants and animals.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera, as well as representatives of the order Acarina.

The good pesticidal activity of the proposed compounds of the formula I according to the invention corresponds to a mortality of at least 50–60% of the above pests.

In addition to their very effective action against flies, e.g. *Musca domestica*, and mosquito larvae, the compounds of formula I are particularly suitable for controlling plant-destructive feeding insects in ornamentals and crops of useful plants, especially in cotton (e.g. against *Spodoptera littoralis* and *Heliothis virescens*) and in crops of vegetables (e.g. against *Leptinotarsa decemlineata* and *Pieris brassicae*). The larvicidal and ovicidal action of the compounds of formula I is to be particularly highlighted. If compounds of formula I are ingested by adult insect stages with the feed, then a diminished oviposition and/or reduced hatching rate is observed in many insects, especially in Coleoptera, e.g. *Anthonomus grandis*.

The compounds of formula I can also be used for controlling ectoparasites such as *Lucilia sericata*, and ticks, in domestic animals and productive livestock, e.g. by treating animals, cowsheds, barns, stables etc., and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and *Bacillus thuringiensis* preparations.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactnats can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of the formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The compositions may also contain further ingredients, such as stabilisers, antifoams, viscosity regulators, binders, tackifiers as well as fertilisers or other active ingredients in order to obtain special effects.

EXAMPLE 1 a) Preparation of the Starting 3-chloro-4-(1,1,2,3,3,3-hexafluoropropoxy)-5-(trifluoromethyl)aniline 42.2 g of 3-chloro-4-(1,1,2,3,3,3-hexafluoropropoxy)-5-(trifluoromethyl)acetaminobenzene are boiled for 16 hours at reflux in a mixture of 200 ml of concentrated hydrochloric acid and 400 ml of ethanol. The bulk of the solvent is then distilled off and the residue is made alkaline and extracted with ether. The ethereal extract is dried over sodium sulfate and the solvent is removed by evaporation in vacuo. Fractional distillation of the residue, affords the title compound as a yellowish oil with a boiling point of 115°–120° C./$4 \cdot 10^{-2}$ torr (a compound of formula II).

b) Preparation of N-[3-chloro-4-(hexafluoropropoxy)-5-trifluoromethyl]-N'-2,6-difluorobenzoylurea A reactor is charged with 3.6 g of the 3-chloro-4-(hexafluoropropoxy)-5-(trifluoromethyl)aniline obtained in a) in 10 ml of dry diethyl ether. With stirring, 1.82 g of 2,6-difluorobenzoylisocyanate are added dropwise. After 3 hours the crystalline precipitate formed is isolated by filtration and washed with a small quantity of ether, affording white crystals of the title compound of the formula

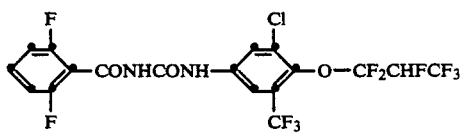

with a melting point of 162°–163° C. (compound 1).

The following compounds of formula I are also obtained by the procedures described above:

| Compound | | mp. [°C.] |
|---|---|---|
| 2 | Cl–[ring]–CONHCONH–[ring(F,CF$_3$)]–O–CF$_2$CHFCF$_3$ (F on left ring) | 166–168 |
| 3 | Cl–[ring]–CONHCONH–[ring(Cl,CF$_3$)]–O–CF$_2$CHFCF$_3$ | 149.5–151 |
| 4 | F–[ring]–CONHCONH–[ring(Cl,CF$_3$)]–O–CF$_2$CHFCF$_3$ | 118–120 |
| 5 | Cl,Cl–[ring]–CONHCONH–[ring(Cl,CF$_3$)]–O–CF$_2$CHFCF$_3$ | 191.5–193 |

EXAMPLE 2 a) Preparation of the Startting 3-bromo-4-(1,1,2,3,3,3-hexafluoropropoxy)-5-(trifluoromethyl)aniline 22.7 g of 3-bromo-4-(1,1,2,3,3,3-hexafluoropropoxy)-5-(trifluoromethyl)acetaminobenzene are heated at reflux for 4 hours in a mixture of 100 ml of concentrated hydrochloric acid and 300 ml of ethanol. The bulk of the solvent is then distilled off, the residue is made alkaline with 10% sodium hydroxide solution and extracted with ether. The ethereal extract is dried over sodium sulfate and the solvent is removed in vacuo. Fractional distillation of the residue affords the title compound as a yellowish oil with a boiling point of 115°–120° C./$5 \cdot 10^{-2}$ torr (a compound of formula II).

b) Preparation of N-[3-bromo-4-(hexafluoropropoxy)-5-trifluoromethyl]-N'-2,6-difluorobenzoylurea 3.5 g of the 3-bromo-4-(hexafluoropropoxy)-5-(trifluoromethyl)aniline obtained in a) in 10 ml of dry diethyl ether are charged to a reactor. With stirring, 1.52 g of 2,6-difluorobenzoylisocyanate are added dropwise at room temperature. After 3 hours, the crystalline precipitate is isolated by filtration and washed with a small quantity of ether, affording white crystals of the title compound of the formula

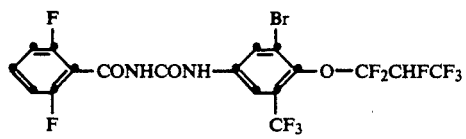

with a melting point of 145°-147° C. (compound 6).

The following compounds of formula I are also prepared in corresponding manner:

| Compound | | mp. [°C.] |
|---|---|---|
| 7 | 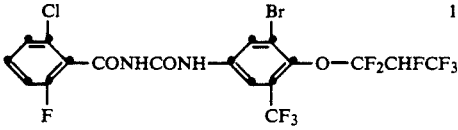 | 183.5-185 |
| 8 | 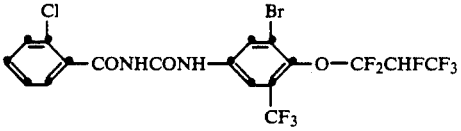 | 141-142 |
| 9 | 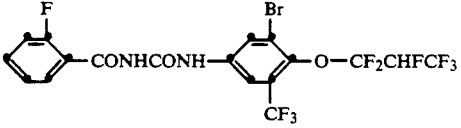 | |
| 10 | 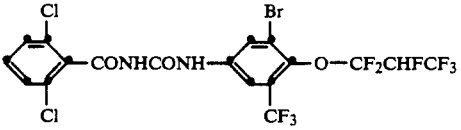 | |

EXAMPLE 3

Formulation Examples for Active Ingredients of the Formula I According to Examples 1 and 2 or Combinations thereof with other Insecticides or Acaricides (Throughout, Percentages are by Weight)

| 1. Wettable powders | a) | b) | c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
|---|---|
| compound of formula I or combination | 10% |
| octylphenol polyethylene glycol ether (4-5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | a) | b) |
|---|---|---|
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 4

Action Against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I obtained according to Examples 1 and 2 have good activity in this test.

EXAMPLE 5

Action Against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of the formula I according to Examples 1 and 2 exhibit good activity against *Lucilia sericata*.

EXAMPLE 6

Action Against *Aedes aegypti*

A concentration of 400 ppm is obtained by pipetting a specific amount of a 0.1% solution of the test compound in acetone onto the surface of 150 ml of water in a beaker. After the acetone has evaporated, 30 to 40 two-day-old larvae of *Aedes aegypti* are put into the beaker containing the test compound. Mortality counts are made after 1, 2 and 5 days.

In this test, compounds of Examples 1 and 2 exhibit good activity against *Aedes aegypti*.

EXAMPLE 7

Insecticidal Action Against Feeding Insects

Cotton plants (about 20 cm high) are sprayed with aqueous emulsions (obtained from a 10% emulsifiable concentrate) containing the respective test compound in concentrations of 0.75 to 400 ppm. After the spray coating has dried, the cotton plants are populated with *Spodoptera littoralis* and *Heliothis virescens* larvae in the $L_3$-stage. The test is carried out at 24° C. and 60% relative humidity. At 24 hour intervals, a mortality count is made and the larva are also examined for inhibition of development and shedding.

In this test, 80–100% kill against Spodoptera is effected with compounds 1, 2 and 4 at 0.75 ppm and with compounds 3, 6, 7 and 8 at 3.0 ppm. The following compounds effect 80–100% kill against Heliothis: compounds 1 and 6 at 3.0 ppm, compounds 2 and 7 at 12.5 ppm, compounds 3 and 8 at 50 ppm, and compound 4 at 400 ppm.

EXAMPLE 8

Action Against *Spodoptera littoralis* and *Heliothis virescens* (larvae and eggs)

Three cotton plants each having a height of about 15–20 cm and grown in pots are treated with a sprayable liquid preparation of the test compound in a concentration of 400 ppm. After the spray coating has dried, the potted plants are placed in a metal container having a capacity of about 20 liters and covered with a glass plate. The humidity in the interior of covered container is regulated such that no water of condensation forms. Direct light falling on the plants is avoided. The three plants are then infested altogether with:

a) 50 larvae of *Spodoptera littoralis* or *Heliothis virescens* in the $L_1$-stage;

b) 20 larvae of *Spodoptera littoralis* or *Heliothis virescens* in the $L_3$-stage;

c) 2 eggs deposits of *Spodoptera littoralis* or *Heliothis virescens*. (The producedure is that two leaves of each plant are put into a plexiglass cylinder sealed at both ends with muslin. Two egg deposits of Spodoptera, or a part of a cotton leaf with eggs of Heliothis deposited thereon, are added to the leaves sealed in the cylinder.)

Evaluation in comparison with untreated controls is made after 4 to 5 days, taking into account the following criteria:

a) the number of still living larvae,
b) inhibition of larval development and shedding,
c) feeding damage (shredding and perforation damage),
d) hatching rate (number of larvae hatched from the eggs).

In this test, the compounds of Formula I according to Examples 1 and 2 exhibit good overall activity.

EXAMPLE 9

Ovicidal Action Against *Spodoptera littoralis*

Eggs of *Spodoptera littoralis* deposited on filter paper are cut out of the paper and immersed in a 0.05% by weight solution of each compound to be tested in a 1:1 mixture of acetone-water. The treated deposits are then removed from this mixture and kept in plastic dishes at 28° C. and 60% humidity. The hatching rate, i.e. the number of larvae which have developed from the treated eggs, is determined after 5 days.

The compounds of formula I according to Examples 1 and 2 show good activity in this test.

EXAMPLE 10

Ovicidal Action Against *Epilachna varivestis*

A mixture is prepared from 20% by weight of test compound, 70% by weight of xylene and 10% by weight of a mixture of a reaction product of an alkyl phenol with ethylene oxide and calcium dodecylbenzenesulfonate. An aqueous emulsion containing 800 ppm of test compound are prepared from this concentrate.

100 eggs of *Epilachna varivestis* (Mexican bean beetle), freshly deposited on leaves of *Phaseolus vulgaris*, are moistened with the above described aqueous emulsion (concentration: 800 ppm) and dried lightly. The treated egg deposits are kept in a ventilated container until the simultaneously deposited untreated controls have hatched.

The percentage kill is evaluated under a stereoscopic microscope.

The compounds of Formula I according to Examples 1 and 2 show good activity in this test.

EXAMPLE 11

Ovicidal Action Against *Heliothis virescens* and *Leptiotarsa decemlineata*

Corresponding amounts of a wettable powder formulation containing 25% by weight of the test compound are mixed with sufficient water to produce an aqueous emulsion with an active ingredient concentration of 800 ppm. One day-old egg deposits of Heliothis on cellophane and egg deposits of Leptinotarsa on potato leaves are immersed in these emulsions for 3 minutes and then collected by suction on round filters. The treated deposits are placed in petri dishes and kept in the dark. The hatching rate in comparison with untreated controls is determined after 6 to 8 days.

Compounds of formula I according to Examples 1 and 2 show good activity in this test.

EXAMPLE 12

Ovicidal Action Against *Laspeyresia pomonella* (eggs)

Egg deposits of *Laspeyrasia pomonella* not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

The compounds of formula I according to Examples 1 and 2 exhibit good activity in this test.

EXAMPLE 13

Action Against *Anthonomus grandis* (adults)

Two cotton plants in the 6-leaf stage, in pots, are each sprayed with a wettable aqueous emulsion formulation containing the test compound in a concentration of 12.5 ppm. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

In this test, compounds 1, 2, 6 and 7 of Example 1 effect 80–100% kill (mortality).

EXAMPLE 14

Action Against Plant-destructive Acarids: *Tetranychus urticae* (OP-sensitive) and *Tetranychus cinnabarinus* (OP-tolerant)

16 hours before the test for acaricidal action, the primary leaves of *Phaseolus vulgaris* plants are infected with an infested piece of leaf from a mass culture of *Tetranychus urticae* (OP-sensitive) and *Tetranychus cinnabarinus* (OP-tolerant). (The tolerance refers to diazinone). The treated infested plants are sprayed to drip point with a test solution containing 400 ppm of the compound to be tested. A count of the number of living and dead imagines and larvae (all mobile stages) is made under a steroscopic microscope after 24 hours and again after 7 days. One plant is used for each test substance and test species. During the test run, the plants are kept in greenhouse compartments at 25° C.

In this test, the compounds of formula I according to Examples 1 and 2 show good activity against *Tetranychus urticae* and *Tetranychus cinnabarinus*.

EXAMPLE 15

Influence on the Reproduction of *Anthonomous grandis*

*Anthonomous grandis* adults which are not more than 24 hours old after hatching are transferred in groups of 25 to barred cages. The cages are then immersed for 5 to 10 seconds in an acetonic solution containing 800 ppm of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

The compounds of the formula I according to Examples 1 and 2 exhibit a good reproduction inhibiting effect in this test.

What is claimed is:

1. A compound of the formula I

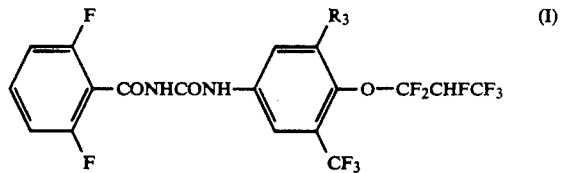

wherein $R_3$ is fluorine, chlorine or bromine.

2. A compound according to claim 1 of the formula

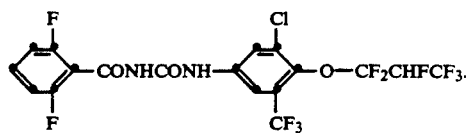

3. A compound according to claim 1 of the formula

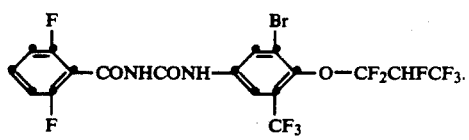

4. A pesticidal composition which comprises an effective amount of a compound as claimed in claim 1, together with a suitable carrier or other adjuvant.

* * * * *